United States Patent [19]

Moffett

[11] 4,075,202

[45] Feb. 21, 1978

[54] S-TRIAZOLO-1,5-BENZODIAZPINE-4-ONES
[75] Inventor: Robert Bruce Moffett, Kalamazoo, Mich.
[73] Assignee: The Upjohn Company, Kalamazoo, Mich.
[21] Appl. No.: 401,220
[22] Filed: Sept. 27, 1973
[51] Int. Cl.² .................................. C07D 487/04
[52] U.S. Cl. .................. 260/239.3 T; 260/239.3 B; 424/244; 424/269
[58] Field of Search .................... 260/239.3 T Primary Examiner—Henry R. Jiles
Assistant Examiner—Robert T. Bond
Attorney, Agent, or Firm—Hans L. Berneis

[57] ABSTRACT

A s-triazolo-1,5-benzodiazepin-4-one selected from the group of compounds of the formulae:

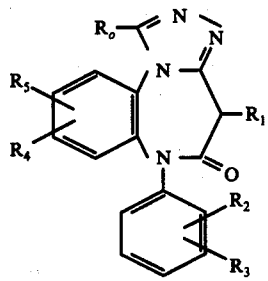

IIIA

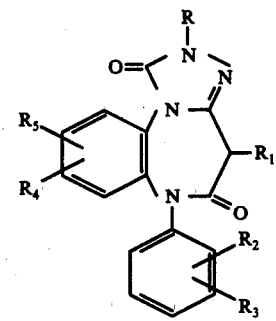

IIIB wherein $R_o$ is hydrogen, alkyl of 1 to 3 carbon atoms, inclusive, hydroxy, hydroxymethyl, and

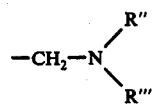

in which R" and R''' are hydrogen or alkyl defined as above, or together

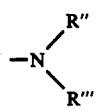

is selected from the group consisting of pyrrolidino, piperidino, morpholino, and N-methylpiperazino; wherein R is hydrogen, alkyl of 1 to 3 carbon atoms, inclusive and

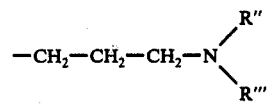

in which R" and R''' are hydrogen or alkyl as defined above or together

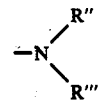

is defined as above; wherein $R_1$ is hydrogen or methyl; wherein $R_2$, $R_3$, $R_4$, and $R_5$ are selected from the group consisting of hydrogen, alkyl alkyl defined as above, halogen, nitro, trifluoromethyl, and alkylthio in which alkyl is defined as above are produced from the corresponding 4-hydrazino-2H-1,5-benzodiazepines-2-ones of the formula (11A)

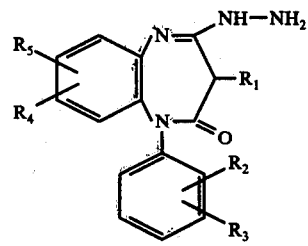

IIA wherein $R_1$, $R_2$, $R_3$, $R_4$, and $R_5$ have the significance of above, with an acetic acid chloride or if $R_o$ is hydrogen with ethyl ortho-formate, and heating to an elevated temperature to give the corresponding 4H-s-triazolo[4,3-a][1,5]benzodiazepin-5(6H)-one which by additional procedures can be converted to the various compounds presented by formula 111A. Compounds of formula 111B are best obtained by reacting a 4-thio-1H-1,5-benzodiazepine-2,4-(3H,5H)-dione (1A)

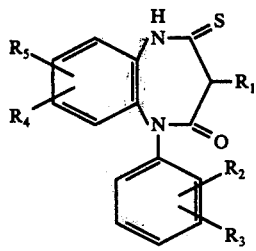

IA with a selected carbazate, followed by heating to an elevated level. Additional steps are necessary to synthesize the various compounds presented by formula 111B. The new compounds of formula 111A and 111B have tranquilizing and sedative activity.

10 Claims, No Drawings

S-TRIAZOLO-1,5-BENZODIAZPINE-4-ONES

BACKGROUND OF THE INVENTION

1. Field of the Invention

This invention is directed to novel organic compounds and is more specifically concerned with triazolo[4,3-a][1,5]benzodiazepines of the formulae IIIA and IIIB below and methods of the production thereof.

The novel compounds and the processes therefor can be illustratively represented as follows:

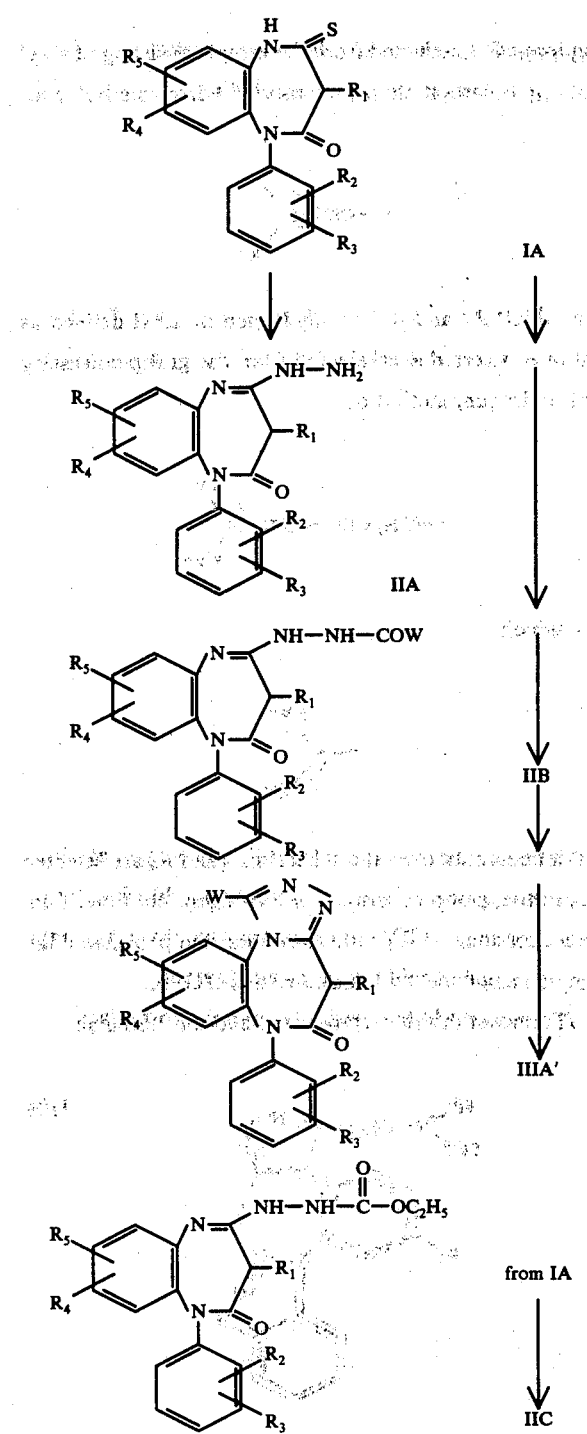

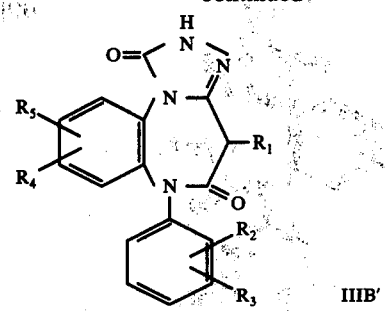

wherein W is alkyl of 1 to 3 carbon atoms, inclusive, —CH₂Cl, or —CH₂OH; wherein $R_1$ is hydrogen or methyl; wherein $R_2$, $R_3$, $R_4$, and $R_5$ are selected from the group consisting of hydrogen, alkyl defined as above, halogen, nitro, trifluoromethyl, and alkylthio in which alkyl is defined as above.

In addition the processes can be performed in a single step from a compound IA with an acid hydrazide or carbazate to give the compounds IIIA' and IIIB' respectively. If a compound IIIA is wanted with hydrogen in the 1-position, ($R_o$ is hydrogen) a compound of formula IA is reacted with triethyl orthoformate.

Further, treatment of a compound of formula IIIA ($R_o$ is hydrogen)

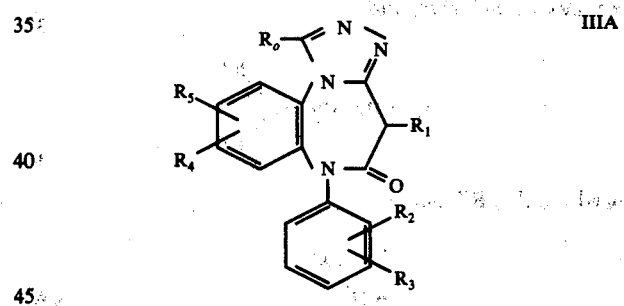

wherein $R_1$, $R_2$, $R_3$, $R_4$ and $R_5$ are defined as above, with chloro or bromosuccinimide gives the corresponding 1-chloro- or 1-bromo derivative of the above compound of formula III which can be converted to other derivatives of formula IIIA as described further on.

The compounds generically embraced by this invention are compounds IIIA and IIIB

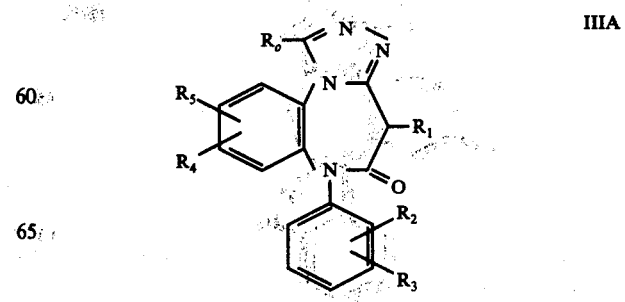

-continued

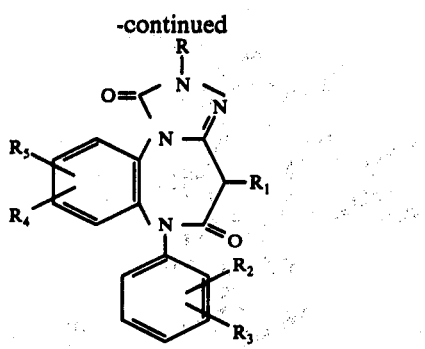
IIIB wherein $R_o$ is hydrogen, alkyl of 1 to 3 carbon atoms, inclusive, hydroxy, hydroxymethyl, and

in which R" and R'" is selected from the group consisting of hydrogen and alkyl defined as above, or together

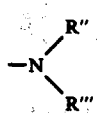

is pyrrolidino, piperidino, morpholino, and N-methylpiperazino; wherein R is hydrogen, alkyl of 1 to 3 carbon atoms, inclusive, and

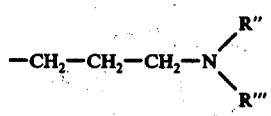

in which R", R'" and

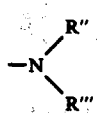

are defined as above, wherein $R_1$ is hydrogen or methyl; wherein $R_2$, $R_3$, $R_4$, and $R_5$ are selected from the group consisting of hydrogen, alkyl defined as above, halogen, nitro, trifluoromethyl, and alkylthio in which alkyl is defined as above, and the pharmacologically acceptable acid addition salts thereof.

The more desirable products are of the formulae

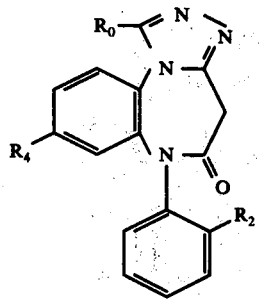
IIIC

-continued

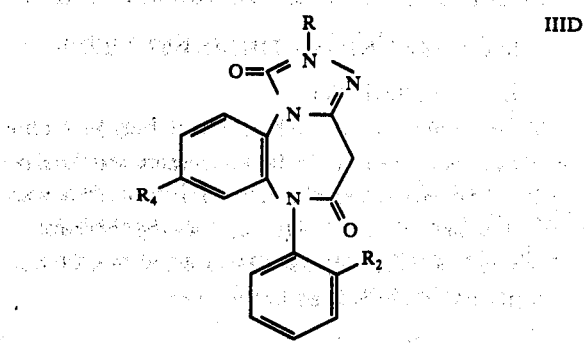
IIID wherein $R_o$ is selected from the group consisting of alkyl of 1 to 3 carbon atoms, inclusive, hydroxymethyl, and

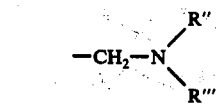

in which R" and R'" are hydrogen or alkyl defined as above; wherein R is selected from the group consisting of hydrogen, methyl or

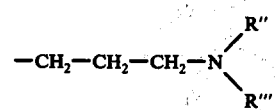

in which

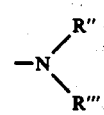

is defined as above; and wherein $R_2$ and $R_4$ are selected from the group consisting of hydrogen, chlorine, fluorine, bromine, $-CF_3$ and nitro, and the pharmacologically acceptable acid addition salts thereof.

The most desirable products have the formulae:

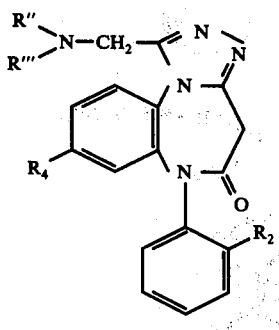
IIIE

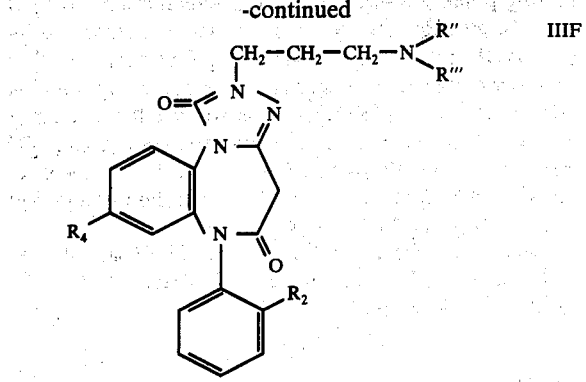

wherein R" and R'" are selected from the group consisting of hydrogen and alkyl of 1 to 3 carbon atoms, inclusive; and wherein $R_2$ and $R_4$ are selected from the group consisting of hydrogen and chlorine.

The process of this invention comprises: treating a compound of formula IA with hydrazine to hydrazine hydrate in methanol or ethanol to give the corresponding compound of formula IIA; treating IIA with a chloroacyl of the formula

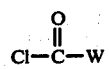

wherein W is alkyl of 1 to 3 carbon atoms —$CH_2OH$ or —$CH_2Cl$; to give the corresponding compound of formula IIB which is cyclized by applying heat to give IIIA'.

If a compound IIIA is desired in which $R_o$ is hydrogen the step IIA→IIB is generally performed with triethylorthoformate.

The reaction from IA to IIIA' can also be performed in one step by reacting compound IA with a selected hydrazide of the formula

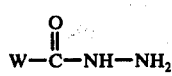

wherein W is defined as above, in a higher boiling alcohol, e.g., n-butanol, n-hexanol, n-octanol, or the like, at a temperature between 115° to the reflux temperature of the reaction mixture.

The triazolone compounds IIIB' are usually synthesized by reacting a compound of formula IA with a carbazate of the formula

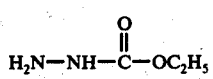

to obtain the compound of formula IIC; heating IIC to 200°-250° to obtain the compound of formula IIIB'.

Additional conventional procedures disclosed in this specification are used to produce other compounds under the general formulae IIIA and IIIB.

DESCRIPTION OF THE PREFERRED EMBODIMENT

Lower alkyl groups of 1 to 3 carbon atoms, inclusive, are exemplified by methyl, ethyl, and propyl.

Sedative effects of the novel compounds are shown by tests known in the art such as:

Chimney test: [Med. Exp. 4, 145 (1961)]: The test determines the ability of mice to back up and out of a vertical glass cylinder within 30 seconds. At the effective dosage, $ED_{50}$, 50% of the mice lose the ability to pass this test.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

The pharmaceutical forms contemplated by this invention include pharmaceutical compositions suited for oral, parenteral and rectal use; e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose, and the like may be used as carriers or for coating purposes. Water and oils, e.g., coconut oil, sesame oil, safflower oil, cottonseed oil, peanut oil may be used for preparing solutions or suspensions of the active drug. Sweetening, coloring, and flavoring agents may be added.

For mammals and birds, food premixes, with starch, oatmeal, dried fishmeat, fishmeal flour, and the like can be prepared.

As tranquilizers, the compounds of formula III can be used in dosages of 0.5 mg. to 30 mg./kg. preferably 5-25 mg./kg. in oral or injectable preparations as described above, to alleviate tension and anxiety in mammals or birds, such as e.g., occurs when animals are shipped. In larger animals above 10 kg. and up, the amounts of active compound per kg. is on the lower side.

Other acid addition salts of the compounds of formula III can be made, such as the fluosilicic acid trichloroacetates salts which are useful mothproofing compounds or the trichloracetates useful as herbicides against Johnson grass, Bermuda grass, yellow foxtail and red foxtail and quack grass.

The starting materials of this invention are compounds of formulae IA, and IB which are both synthesized from compounds of the formula I.

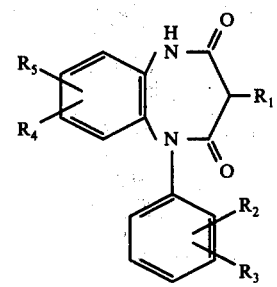

wherein $R_1$ is hydrogen or methyl; and wherein $R_2$, $R_3$, $R_4$, and $R_5$ are selected from the group consisting of hydrogen, alkyl of 1 to 3 carbon atoms, inclusive, halogen, nitro, trifluoromethyl, and alkylthio of 1 to 3 carbon atoms, inclusive, by heating with phosphorus pentasulfide (as shown in Preparation 1).

Compounds of formula I are specifically disclosed in Chemical Abstract 70, 106,576f (1969), Belgium Patent 774872 and U.S. Pat. No. 3,684,798.

The sulfides IA when heated with hydrazine hydrate in methanol, ethanol, or 1- or 2 -propanol provide the starting compounds of formula IB.

In carrying out the process for the preparation of compounds of structure IIIA, a compound of formula IA is treated with hydrazine hydrate in a lower alcohol, e.g., methanol, ethanol, or 1- or 2-propanol. In the preferred embodiment of this invention, hydrazine hydrate is used in excess from 2 to 6 times the stoichiometrically required amount. Methanol or ethanol are preferred as solvent. The reaction can be carried out between 0° to reflux temperature of the mixture, with 20° to 30° C. preferred. The mixture is stirred for 2 to 24 hours to achieve completion of the reaction. The resulting product IIA is separated by conventional procedures, e.g., filtration, extraction, crystallization and/or chromatography.

Compound IIA thus obtained is then treated with a selected acetyl chloride or bromide to give a compound of formula IIB. This reaction is preferably carried out in an inert solvent, e.g., tetrahydrofuran, ether, dioxane or the like, at low temperatures −5° to 10° C., and during a period of 20–75 minutes. At the termination of the reaction the product is separated and purified by conventional procedures, e.g., filtration, extraction, crystallization, and/or chromatography.

Compound IIB by merely heating, preferably in a solvent such as acetic acid, propionic acid, xylene, butanol, between 100°–200° C., during 1 to 8 hours, gives the corresponding compound IIIA', which is isolated and purified by conventional procedures, e.g., filtration, extraction, crystallization, and/or chromatography.

The three steps to obtain compound IIIA can also be performed in one sequence by reacting compound IA with a selected acetyl hydrazide in a higher boiling alcohol, e.g., n-butanol, n-pentanol, n-octanol, and refluxing the mixture at this temperature for 6–48 hours. Again the product is isolated and purified by conventional procedures, e.g., filtration, extraction, crystallization, and/or chromatography.

Compounds of structure IIIB' are obtained by reacting a compound of formula IA with a selected carbazate, or reacting a compound of formula IIA with a selected alkyloxycarbonyl chloride or to obtain the compounds of formula IIC. Compounds IIC when heated to 200°–260° C. provide the compounds of formula IIIB'.

Other substituted compounds of formula IIIA and IIIB can be made from compounds IIIA' or respectively IIIB' by known methods as illustrated further in the examples.

The following examples are illustrative of the processes and products of the present invention, but are not to be construed as limiting.

Preparation 1

8-Chloro-1-phenyl-4-thio-1H-1,5-benzodiazepine-2,4(3H,5H)-dione

A mixture of 12 g. (0.04mole) of 8-chloro-1-phenyl-1H-1,5-benzodiazepin-2,4(3H,5H)-dione and 14 g. (0.065 mole) of phosphorus pentasulfide in 100 ml. of pyridine is heated to reflux for 45 minutes in a nitrogen atmosphere. The dark solution is evaporated to dryness in vacuo. The residue is treated with 100 ml. of sodium chloride solution and then extracted with three 200 ml. portions of methylene chloride. The methylene chloride solution is washed with water and dried over anhydrous sodium sulfate. After filtration and evaporation in vacuo to dryness, the residue is dissolved in a mixture of methylene chloride and methanol and filtered hot. On cooling it gives 11 g. of yellow crystalline material of melting point 263°–266° C. (dec.), which is a mixture of two compounds. Two g. of this mixture is separated by column chromatography on silica gel using 25% ethyl acetate:cyclohexane as an eluent, giving compounds A (800 mg.) and B (400 mg); A is recrystallized from a mixture of methylene chloride and methanol giving 600 mg. of 8-chloro-1-phenyl-4-thio-1H-1,5-benzodiazepine-2,4-(3H,5H)-dione as white crystalline compound of melting point 265°–267° C.

Anal. calcd. for $C_{15}H_{11}ClN_2OS$: C, 59.52; H, 3.66; N, 9.25; Cl, 11.72; S, 10.57. Found: C, 58.81; H, 3.97; N, 9.43; Cl, 11.32; S, 10.72.

Preparation 2

8-Chloro-1-phenyl-4-hydrazino-1,3-dihydro-2H-1,5-benzodiazepine-2-one

To a suspension of 12.9 g. (0.042 mole) of 8-chloro-1-phenyl-4-thio-1H-1,5-benzodiazepine-2,4(3H,5H)-dione in 350 ml. of methanol is added dropwise, 9.6 ml. (0.198 mole) of hydrazine hydrate. A stream of nitrogen is bubbled through the reaction mixture to remove hydrogen sulfide formed during reaction. After complete addition of hydrazine hydrate, the resulting suspension is stirred at room temperature (22°–25° C.) overnight. A white solid is separated by filtration, washed with methanol and dried giving 6 g. of white solid of melting point 91°–93° C. This was recrystallized from methanol giving 4 g. of 8-chloro-1-phenyl-4-hydrazino-1,3-dihydro-2H-1,5-benzodiazepine-2-one as white drystalline solid of melting point 102°–103° C.

The filtrate from above is evaporated to dryness in vacuo giving an orange oil. This oil is dissolved in methanol and on standing, it gives a second crop of desired product, 2.5 g. of melting point 91°–93° C.

Anal. calcd. for $C_{15}H_{13}ClN_4O \cdot 1\frac{1}{2}H_2O$: C, 54.97; H, 4.91; N, 17.10; Cl, 10.82. Found: C, 55.02; H, 4.54; N, 17.03; Cl, 10.91.

Preparation 3

8-Chloro-1-(o-chlorophenyl)-4-thio-1H-1,5-benzodiazepine-2,4-(3H,5H)-dione

In the manner given in Preparation 1, 8-chloro-1-(o-chlorophenyl)-1H-1,5-benzodiazepine-2,4(3H,5H)-dione [C. A. 70, 106,578E (1969)] can be heated with phosphorus pentasulfide in pyridine to give 8-chloro-1-(o-chlorophenyl)-4-thio-1H-1,5-benzodiazepin-2,4-(3H,5H)-dione.

In the manner given in Preparation 1, other 1-phenyl-4-thio-1H-1,5-benzodiazepine-2,4-(3H,5H)-dione starting compounds can be produced. Representative compounds, thus obtained include:

8-bromo-1-(o-bromophenyl)-4-thio-1H-1,5-benzodiazepine-2,4-(3H,5H)-dione;

8-chloro-1-(o-bromophenyl)-4-thio-1H-1,5-benzodiazepine-2,4-(3H,5H)-dione;

8-fluoro-1-(o-bromophenyl)-4-thio-1H-1,5-benzodiazepine-2,4-(3H,5H)-dione;

7-trifluoromethyl-1-(o-bromophenyl)-4-thio-1H-1,5-benzodiazepine-2,4-(3H,5H)-dione;

8-chloro-1-(2-chloro-4-methylphenyl)-4-thio-1H-1,5-benzodiazepine-2,4-(3H,5H)-dione;

8-chloro-1-(o-nitrophenyl)-4-thio-1,5-benzodiazepine-2,4-(3H,5H)-dione;

8-chloro-1-(m-trifluoromethylphenyl)-4-thio-1H-1,5-benzodiazepine-2,4-(3H,5H)-dione;

8-chloro-1-(o-trifluoromethylphenyl)-4-thio-1H-1,5-benzodiazepine-2,4-(3H,5H)-dione;

8-chloromethyl-1-phenyl-4-thio-1H-1,5-benzodiazepine-2,4-(3H,5H)-dione;

7-trifluoromethyl-1-phenyl-4-thio-1H-1,5-benzodiazepine-2,4-(3H,5H)-dione;

8-trifluoromethyl-1-(o-fluorophenyl)-4-thio-1H-1,5-benzodiazepine-2,4-(3H,5H)-dione;

7-methoxy-1-phenyl-4-thio-1H-1,5-benzodiazepine-2,4-(3H,5H)-dione;

8-trifluoromethyl-1-(o-nitrophenyl)-4-thio-1H-1,5-benzodiazepine-2,4-(3H,5H)-dione;

8-trifluoromethyl-1-(m-nitrophenyl)-4-thio-1H-1,5-benzodiazepine-2,4-(3H,5H)-dione;

8-trifluoromethyl-1-(p-nitrophenyl)-4-thio-1H-1,5-benzodiazepine-2,4-(3H,5H)-dione;

and the like.

EXAMPLE 1

8-Chloro-1-methyl-6-phenyl-4H-s-triazolo[4,3-a][1,5]benzodiazepin-5(6H)-one

A solution of 3 g. (0.01 mole) of 8-chloro-1-phenyl-4-thio-1H-1,5-benzodiazepin-2,4-(3H,5H)-dione and 8-chloro-1-phenyl-1H-1,5-benzodiazepin-2,4-(3H,5H)-dithione and 2 g. (0.024 mole) of acethydrazide in 300 ml. of n-butanol is refluxed for 24 hours. During this period nitrogen is bubbled through the reaction mixture. The solution is evaporated to dryness in vacuo and the residue is treated with cold water which gives 2.7 g. of yellow material. This material was found by thin layer chromatography ($SiO_2$, 10% methanol; 90% chloroform) to be a mixture of three compounds and was chromatographed on 300 g. of silica gel using 3% methanol:97% chloroform as an eluting solvent. Fractions 12–19 (100 ml. each) were combined and concentrated giving 1.2 g. of product. This was recrystallized from absolute ethanol giving 800 mg. of white 8-chloro-1-methyl-6-phenyl-4H-s-triazolo[4,3-a][1,5]benzodiazepin-5(6H)-one as white crystalline product of melting point 297°–298° C.

Anal. calcd. for $C_{17}H_{13}ClN_4O$: C, 62.87; H, 4.03; N, 17.28; Cl, 10.91 Found: C, 62.49; H, 4.07; N, 17.54; Cl, 11.14.

EXAMPLE 2

8-Chloro-1-methyl-6-(o-chlorophenyl)-4H-s-triazolo[4,3-a][1,5]benzodiazepin-5(6H)-one In the manner given in Example 1, 8-chloro-1-(o-chlorophenyl)-4-thio-1H-1,5-benzodiazepin-2,4-(3H,5H)-dione can be heated with acethydrazide in n-butanol to give 8-chloro-1-methyl-6-(o-chlorophenyl)-4H-s-triazolo[4,3-a][1,5]benzodiazepin-5(6H)-one.

EXAMPLE 3

8-Chloro-1-methyl-6-(o-fluorophenyl)-4H-s-triazolo[4,3-a][1,5]benzodiazepin-5(6H)-one In the manner given in Example 1, 8-chloro-1-(o-fluorophenyl)-4-thio-1H-1,5-benzodiazepin-2,4-(3H,5H)-dione can be heated with acethydrazide in n-butanol to give 8-chloro-1-methyl-6-(o-fluorophenyl)-4H-s-triazolo[4,3-a][1,5]benzodiazepin-5(6H)-one.

EXAMPLE 4

7-Bromo-1-methyl-6-phenyl-4H-s-triazolo[4,3-a][1,5]benzodiazepin-5(6H)-one

In the manner given in Example 1, 9-bromo-1-phenyl-4-thio-1H-1,5-benzodiazepin-2,4-(3H,5H)-dione can be heated with acethydrazide in n-butanol to give 7-bromo-1-methyl-6-phenyl-4H-s-triazolo[4,3-a][1,5]benzodiazepin-5(6H)-one.

EXAMPLE 5

8-Nitro-1-methyl-6-(o-chlorophenyl)-4H-s-triazolo[4,3-a][1,5]benzodiazepin-5(6H)-one In the manner given in Example 1, 8-nitro-1-(o-chlorophenyl)-4-thio-1H-1,5-benzodiazepin-2,4-(3H,5H)-dione can be heated with acethydrazide in n-butanol to give 8-nitro-1-methyl-6-(o-chlorophenyl)-4H-s-triazolo[4,3-a][1,5]benzodiazepin-5(6H)-one.

EXAMPLE 6

8-Fluoro-1-ethyl-6-phenyl-4H-s-triazolo[4,3-a][1,5]benzodiazepin-5(6H)-one

In the manner given in Example 1, 8-fluoro-1-phenyl-4-thio-1H-1,5-benzodiazepin-2.4-(3H,5H)-dione can be heated with propionic acid hydrazide in n-butanol to give 8-fluoro-1-ethyl-6-phenyl-4H-s-triazolo[4,3-a][1,5]benzodiazepin-5(6H)-one.

EXAMPLE 7

Chloroacetic acid, 2-(7-chloro-4-oxo-5-phenyl-3H-1,5-benzodiazepine-2-yl)hydrazide To a stirred ice-cold mixture of 4 g. (0.0133 mole) of 8-chloro-1,3-dihydro-5-phenyl-4-hydrazino-2H-1,5-benzodiazepine-2-one in 30 ml. of tetrahydrofuran, under nitrogen is added dropwise, a solution of 1.5 g. (0.0133 mole) of chloroacetyl chloride in 5 ml. of tetrahydrofuran. The resulting solution is kept at 0° C. for 35 minutes with stirring and then at room temperature for 1 hour. The above solution is poured on ice, treated with chloroform and neutralized with 5% sodium bicarbonate. A white solid which had separated is recovered on filter, washed with water, then ether, and air-dried giving 4 g. of chloroacetic acid, 2-(7-chloro-4-oxo-5-phenyl-3H-1,5-benzodiazepine-2-yl)hydrazide of melting point 210°–215° C.

EXAMPLE 8

8-Chloro-1-(chloromethyl)-6-phenyl-4H-s-triazolo[4,3-a][1,5]benzodiazepin-5(6H)-one A suspension of 1.5 g. of chloroacetic acid, 2-(7-chloro-4-oxo-5-phenyl-3H-1,5-benzodiazepine-2-yl)hydrazide in 20 ml. glacial acetic acid is immersed in an oil bath which was previously heated to 140° C. The reaction mixture is heated for 4 hours under nitrogen and allowed to cool to room temperature. A white solid precipitates. This precipitate is recovered by filtration, washed with water, ether and air-dried giving 1.1 g. of 8-chloro-1-(chloromethyl)-6-phenyl-4H-s-triazolo[4,3-a][1,5]benzodiazepin-5(6H)-one of melting point 282°–285° C. (dec.). An analytical sample, crystallized from methanol:methylene chloride had a melting point of 306°–308° C. (dec.).

Anal. calcd. for $C_{17}H_{12}Cl_2N_4O$: C, 56.84; H, 3.37; N, 15.60; Cl, 19.74. Found: C, 56.81; H, 3.53; N, 15.62; Cl, 20.30.

EXAMPLE 9

8-Chloro-1-[(dimethylamino)methyl]-6-phenyl-4H-s-triazolo[4,3-a][1,5]benzodiazepine-5(6H)-one To a cold suspension of 1.07 g. of 8-chloro-1-(chloromethyl)-6-phenyl-4H-s-triazolo[4,3-a][1,5]benzodiazepine-5(6H)-one in 30 ml. of tetrahydrofuran is added 5 g. of dimethyl amine in methanol and 0.5 g. of potassium iodide under nitrogen. The resulting mixture is stirred at room temperature for 4 hours. The above solution is evaporated to dryness in vacuo. The resulting residue is treated with 5.1 g. sodium carbonate and extracted with chloroform (twice). The chloroform extract is washed with water, dried over anhydrous sodium sulfate and evaporated to give white oil. This on trituration with ethyl acetate gives 980 mg. of 8-chloro-1-[(dimethylamino)methyl]-6-phenyl-4H-s-triazolo[4,3-a][1,5]benzodiazepin-5(6H)-one of melting point 232°–234° C. An analytical sample, crystallized from ethyl acetate, had a melting point of 235°–236° C.

Anal. calcd. for $C_{19}H_{18}ClN_5O$: C, 62.04; H, 4.93; N, 19.05; Cl, 9.64. Found: C, 61.79; H, 4.97; N, 19.84; Cl, 9.50.

EXAMPLE 10

2-Hydrazino-7-chloro-4,5-dihydro-5-[o-chlorophenyl]-3H-1,5-benzodiazepine-4-one

In the manner given in Example 7, 8-chloro-1-(o-chlorophenyl)-4-thio-1H-1,5-benzodiazepin-2,4-(3H,5H)-dione can be heated in n-propanol with hydrazine hydrate to give 4-hydrazino-8-chloro-4,5-dihydro-1-(o-chlorophenyl)-3H-1,5-benzodiazepin-2-one.

EXAMPLE 11

Chloroacetic acid 2-[7-chloro-4-oxo-5-(o-chlorophenyl)-3H-1,5-benzodiazepin-2-yl]hydrazide In the manner given in Example 8, 4-hydrazino-8-chloro-4,5-dihydro-1-(o-chlorophenyl)-3H-1,5-benzodiazepine-2-one can be reacted with chloroacetyl chloride in tetrahydrofuran to give chloroacetic acid 2-[7-chloro-4-oxo-5-(o-chlorophenyl-3H-1,5-benzodiazepin-2-yl)hydrazide.

EXAMPLE 12

8-Chloro-1-(chloromethyl)-6-(o-chlorophenyl)-4H-s-triazolo[4,3-a][1,5]benzodiazepin-5(6H)-one In the manner given in Example 9, 2-[7-chloro-4-oxo-5-(o-chlorophenyl)-3H-1,5-benzodiazepine-2-yl]hydrazide can be heated to 140°–150° C. to give 8-chloro-1-(chloromethyl)-6-(o-chlorophenyl)-4H-s-triazolo[4,3-a][1,5]benzodiazepin-5(6H)-one.

EXAMPLE 13

8-Chloro-1-[(dimethylamino)methyl]-6-(o-chlorophenyl)-4H-s-triazolo[4,3-a][1,5]benzodiazepine-5(6H)-one In the manner given in Example 10, 8-chloro-1-(chloromethyl)-6-phenyl-4H-s-triazolo[4,3-a][1,5]benzodiazepine-5(6H)-one can be reacted with dimethylamine to give 8-chloro-1-[(dimethylamino)methyl]-6-(o-chlorophenyl)-4H-s-triazolo[4,3-a][1,5]benzodiazepin-5(6H)-one.

EXAMPLE 14

8-Chloro-1-[(diethylamino)methyl]-6-(o-chlorophenyl)-4H-s-triazolo[4,3-a][1,5]benzodiazepine-5(6H)-one In the manner given in Example 10, 8-chloro-1-(chloromethyl)-6-phenyl-4H-s-triazolo[4,3-a][1,5]benzodiazepine-5(6H)-one can be reacted with diethylamine to give 8-chloro-1-[(diethylamino)methyl]-6-(o-chlorophenyl)-4H-s-triazolo[4,3-a][1,5]benzodiazepin-5(6H)-one.

EXAMPLE 15

8-Chloro-1-[(methylamino)methyl]-6-(o-chlorophenyl)-4H-s-triazolo[4,3-a][1,5]benzodiazepine-5(6H)-one In the manner given in Example 10, 8-chloro-1-(chloromethyl)-6-phenyl-4H-s-triazolo[4,3-a][1,5]benzodiazepine-5(6H)-one can be reacted with methylamine to give 8-chloro-1-[(methylamino)methyl]-6-(o-chlorophenyl)-4H-s-triazolo[4,3-a][1,5]benzodiazepin-5(6H)-one.

EXAMPLE 16

8-Chloro-1-[(amino)methyl]-6-(o-chlorophenyl)-4H-s-triazolo[4,3-a][1,5]benzodiazepine-5(6H)-one In the manner given in Example 10, 8-chloro-1-(chloromethyl)-6-phenyl-4H-s-triazolo[4,3-a][1,5]benzodiazepine-5(6H)-one can be reacted with ammonia to give 8-chloro-1-[aminomethyl]-6-(o-chlorophenyl)-4H-s-triazolo[4,3-a][1,4]benzodiazepin-5(6H)-one.

EXAMPLE 17

8Chloro-1-hydroxymethyl-6-phenyl-4H-s-triazolo[4,3-a][1,5]benzodiazepine-5(6H)one In the manner given in Example 1, 8-chloro-1-phenyl-4-thio-1H-1,5-benzodiazepin-2,4-(3H,5H)-dione can be heated with hydroxyacetyl hydrazide in n-butanol to give 8-chloro-1-hydroxymethyl-6-phenyl-4H-s-triazolo[4,3-a][1,5]benzodiazepine-5(6H)one.

In the same manner as above but heating with α-hydroxypropionyl hydrazide will give 8-chloro-1-(α-hydroxyethyl)-6-phenyl-4H-s-triazolo[4,3-a][1,5]benzodiazepine.

EXAMPLE 18

8-Chloro-6-phenyl-4H-s-triazolo[4,3-a][1,5]benzodiazepine-5(6H)one.

2-Hydrazino-7-chloro-4,5-dihydro-5-phenyl-3H-1,5-benzodiazepin-4-one is heated with triethyl orthoformate and concentrated sulfuric acid. The mixture is stirred for 30 minutes to give 8-chloro-6-phenyl-4H-s-triazolo[4,3-a][1,5]benzodiazepine-5(6H)-one.

In the manner given in the preceding examples other compounds of formula IIIA can be produced. Compounds, thus obtained, include:

8-methoxy-1-propyl-6-phenyl-4H-s-triazolo[4,3-a][1,5]benzodiazepine-5(6H)-one;

1-ethyl-6-phenyl-4H-s-triazolo[4,3-a][1,5]benzodiazepine;

1-methyl-6-(o-methoxyphenyl)-4H-s-triazolo[4,3-a][1,5]benzodiazepine-5(6H)-one;

1-methyl-6-(m-methoxyphenyl)-4H-s-triazolo[4,3-a][1,5]benzodiazepine-5(6H)-one;

8-chloro-1-ethyl-6-(m-chlorophenyl)-4H-s-triazolo[4,3-a][1,5]benzodiazepine-5(6H)-one;

8-chloro-1-methyl-6-(o-methylphenyl)-4H-s-triazolo[4,3-a][1,5]benzodiazepine-5(6H)-one;

8-chloro-1-ethyl-6-(2,4-dimethylphenyl)-4H-s-triazolo[4,3-a][1,5]benzodiazepine-5(6H)-one;

8-fluoro-1-methyl-6-phenyl-4H-s-triazolo[4,3-a][1,5]benzodiazepine-5(6H)-one;

8-chloro-1-propyl-6-(2-methyl-4-chlorophenyl)-4H-s-triazolo[4,3-a][1,5]benzodiazepine-5(6H)-one;

8-bromo-1-methyl-6-phenyl-4H-s-triazolo[4,3-a][1,5]benzodiazepine-5(6H)-one;

8-chloro-6-(o-ethylphenyl)-4H-s-triazolo[4,3-a][1,5]benzodiazepine-5(6H)-one;

8-trifluoromethyl-1-ethyl-6-phenyl-4H-s-triazolo[4,3-a][1,5]benzodiazepine-5(6H)-one;

1-(diethylamino)methyl-8-bromo-6-phenyl-4H-s-triazolo[4,3-a][1,4]benzodiazepine-5(6H)-one;

1-(ethylamino)methyl-8-trifluoromethyl-6-phenyl-4H-s-triazolo[4,3-a][1,5]benzodiazepine-5(6H)-one;

1-aminomethyl-8-trifluoromethyl-6-phenyl-4H-s-triazolo[4,3-a][1,5]benzodiazepine-5(6H)-one;
1-aminomethyl-8-trifluoromethyl-6-o-chlorophenyl-4H-s-triazolo[4,3-a][1,5]benzodiazepine-5(6H)-one;
and the like.

EXAMPLE 19

Ethyl, 3-[7-chloro-4,5-dihydro-4-oxo-5-phenyl-3H-1,5-benzodiazepin-2-yl]carbazate A solution of 5.5 g. (0.02 mole) of crude 8-chloro-1-phenyl-4-thio-1H-1,5-benzodiazepin-2,4-(3H,5H)-dione (Preparation 1) and 5g. (0.06 mole) of ethyl carbazate in 200 ml. of n-butanol is refluxed for 24 hours. During this period nitrogen is bubbled through the reaction mixture. The solution is evaporated to dryness in vacuo giving 6 g. of oily material which is a mixture of four compounds. This mixture is dissolved in methylene chloride, washed with water and dried over anhydrous potassium carbonate. After filtration and evaporation is gives a yellow gum which on trituration with anhydrous ether gives 6 g. of a yellow solid. This was found by thin layer chromatography to still be a mixture of four compounds and is used without purification for Example 20.

EXAMPLE 20

8-Chloro-6-phenyl-1H-s-triazolo[4,3-a][1,5]-benzodiazepine-1,5-(2H,6H)-dione

Two g. of the mixture from Example 19 is heated at 240° C. in an oil bath for 30 minutes under nitrogen. The resulting brown oil solidified on cooling. The solid is dissolved in absolute ethanol by warming it on a steam bath and filtered hot. On cooling it gives 900 mg. of brown solid which is shown by thin layer chromatography to be a mixture. This mixture is separated by column chromatography on silica gel using 3% methanol:97% chloroform as an eluting solvent. This afforded 300 mg. of white solid which was recrystallized from ethyl acetate and Skellysolve B hexanes to give 200 mg. of 8-chloro-6-phenyl-1H-s-triazolo[4,3-a][1,5]benzodiazepine-1,5-(2H,6H)-dione as white crystals of melting point 110°–112° C.

Anal. calcd. for $C_{16}H_{11}ClN_4O_2$: C, 58.82; H, 3.39; N, 17.14; Cl, 10.85. Found: C, 58.71; H, 4.69; N, 17.11; Cl, 11.07.

EXAMPLE 21

2-Methyl-8-chloro-6-phenyl-1H-s-triazolo[4,3-a][1,5]benzodiazepine-1,5-(2H,6H)-dione and its hydrochloride A solution of 8-chloro-6-phenyl-1H-s-triazolo[4,3-a][1,5]benzodiazepin-1,5-(2H,6H)-dione in dry dimethylformamide in a nitrogen atmosphere can be treated first with sodium hydride (a 58% suspension of NaH in mineral oil) and then with methyl iodide in ether. Stirring at room temperature and chromatographing will give 8-chloro-2-methyl-6-phenyl-1H-triazolo[4,3-a][1,5]benzodiazepin-1,5-(2H,6H)-dione. This can be converted with etheral hydrogen chloride to its hydrochloride salt to give 8-chloro-2-methyl-6-phenyl-1H-s-triazolo[4,3-a][1,5]benzodiazepin-1,5(2H,6H)-dione hydrochloride.

8-Chloro-2-methyl-6-phenyl-1H-s-triazolo[4,3-a][1,5]benzodiazepin-1,5-(2H,6H)-dione can also be obtained by reacting 8-chloro-6-phenyl-1H-s-triazolo[4,3-a][1,5]benzodiazepin-1,5-(2H,6H)-dione in methylene chloride and methanol with diazomethane at about 0°–5° C.

EXAMPLE 22

8-Chloro-2-ethyl-6-phenyl-1H-s-triazolo[4,3-a][1,5]benzodiazepin-1,5-(2H,6H)dione In the manner given in Example 21, 8-chloro-6-phenyl-1H-s-triazolo[4,3-a][1,5]benzodiazepin-1,5-(2H,6H)-dione can be reacted with sodium hydride and then with ethyl bromide to give 8-chloro-2,4-dihydro-2-ethyl-6-phenyl-1H-s-triazolo[4,3-a][1,4]benzodiazepin-1-one.

EXAMPLE 23

8-Chloro-2-[(dimethylamino)propyl]-6-phenyl-1H-s-triazolo[4,3-a][1,5]benzodiazepin-1,5-(2H,6H)-dione In the manner given in Example 21 8-chloro-6-phenyl-1H-s-triazolo[4,3-a][1,5]benzodiazepin-1,5-(2H,6H)-dione can be reacted with potassium hydride and then with dimethylamino propyl chloride to give 8-chloro-2-[(dimethylaminopropyl]-6-phenyl-1H-s-triazolo[4,3-a][1,5]benzodiazepin-1,5-(2H,6H)-dione.

EXAMPLE 24

8-Chloro-2-[(diethylamino)propyl]-6-phenyl-1H-s-triazolo[4,3-a][1,5]benzodiazepin-1,5-(2H,6H)-dione In the manner given in Example 21, 8-chloro-6-phenyl-1H-s-triazolo[4,3-a][1,5]benzodiazepin-1,5-(2H,6H)-dione can be reacted with sodium hydride and then with (diethylamino)-propyl bromide to give 8-chloro-2-[(diethylamino)propyl]-6-phenyl-1H-s-triazolo[4,3-a][1,5]benzodiazepin-1,5-(2H,6H)-dione.

EXAMPLE 25

Ethyl-3-[7-chloro-4,5-dihydro-4-oxo-5-(o-chlorophenyl)-3H-1,5-benzodiazepin-2-yl]carbazate In the manner given in Example 19, 7-chloro-5-(o-chlorophenyl)-2-thio-1H-1,5-benzodiazepin-2,4-(3H,5H)-dione in n-butanol can be refluxed with ethyl carbazate to give ethyl 3-[7-chloro-4,5-dihydro-4-oxo-5-(o-chlorophenyl)-3H-1,5-benzodiazepin-2-yl]carbazate.

EXAMPLE 26

8-Chloro-6-(o-chlorophenyl)-1H-s-triazolo[4,3-a][1,5]benzodiazepin-1,5-(2H,6H)-dione In the manner given in Example 20, 3-[7-chloro-4,5-dihydro-4-oxo-5-(o-chlorophenyl)-3H-1,5-benzodiazepin-2-yl]carbazate can be heated to about 250° C. to give 8-chloro-6-(o-chlorophenyl)-1H-s-triazolo[4,3-a][1,5]benzodiazepin-1,5(2H,6H)-dione.

EXAMPLE 27

8-Chloro-2-[(dimethylamino)propyl]-6-(o-chlorophenyl)-1H-s-triazolo[4,3-a][1,5]benzodiazepin-1,5-(2H,6H)-dione In the manner given in Example 21, 8-chloro-6-(o-chlorophenyl)-1H-s-triazolo[4,3-a][1,4]benzodiazepin-1,5-(2H,6H)-dione can be reacted with sodium hydride and then with (dimethylaminopropyl bromide to give 8-chloro-2-[(dimethylamino)propyl]-6-(o-chlorophenyl)-1H-s-triazolo[4,3-a][1,5]benzodiazepin-1,5-(2H,6H)-dione.

EXAMPLE 28

8-Chloro-2-[dipropylamino)propyl]-6-(o-chlorophenyl)-1H-s-triazolo[4,3-a][1,5]benzodiazepin-1,5-(2H,6H)-dione In the manner given in Example 21, 8-chloro-6-(o-chlorophenyl)-1H-s-triazolo[4,3-a][1,5]benzodiazepin-1,5-(2H,6H)-dione can be reacted with sodium hydride and then with dipropylamino propyl chloride to give 8-chloro-2-[(dipropylamino)propyl]-6-(o-chlorophenyl)-1H-s-triazolo[4,3-a][1,5]benzodiazepin-1,5-(2H,6H)-dione.

EXAMPLE 29

Ethyl-3-[7-fluoro-4,5-dihydro-4-oxo-5-(chlorophenyl)-3H-1,5-benzodiazepin-2-yl]carbazate In the manner given in Example 19, 7-fluoro-5-(o-chlorophenyl)-2-thio-1H-1,5-benzodiazepin-2,4-(3H,5H)-dione in n-butanol can be refluxed with ethyl carbazate to give ethyl 3-[7-fluoro-4,5-dihydro-4-oxo-5-(o-chlorophenyl)-3H-1,5-benzodiazepin-2-yl]carbazate.

EXAMPLE 30

8-Fluoro-6-(o-chlorophenyl)-1H-s-triazolo[4,3-a][1,5]benzodiazepin-1,5-(2H,6H)-dione In the manner given in Example 20, 3-[7-fluoro-4,5-dihydro-4-oxo-5-(o-chlorophenyl)-3H-1,5-benzodiazepin-2-yl]carbazate can be heated to about 250° C. to give 8-fluoro-6-(o-chlorophenyl)-1H-s-triazolo[4,3-a][1,5]benzodiazepin-1,5-(2H,6H)-dione.

EXAMPLE 31

Ethyl-3-[7-nitro-4,5-dihydro-4-oxo-5-(o-chlorophenyl)-3H-1,5-benzodiazepin-2-yl]carbazate In the manner given in Example 19, 7-nitro-5-(o-chlorophenyl)-2-thio-1H-1,5-benzodiazepin-2,4-(3H,5H)-dione in n-butanol can be refluxed with ethyl carbazate to give ethyl 3-[7-nitro-4,5-dihydro-4-oxo-5-(o-chlorophenyl)-3H-1,5-benzodiazepin-2-yl]carbazate.

EXAMPLE 32

8-Nitro-6-(o-chlorophenyl)-1H-s-triazolo[4,3-a][1,5]benzodiazepin-1,5-(2H,6H)-dione In the manner given in Example 20, 3-[7-nitro-4,5-dihydro-4-oxo-5-(o-chlorophenyl)-3H-1,5-benzodiazepin-2-yl]carbazate can be heated to about 250° C. to give 8-nitro-6-(o-chlorophenyl)-1H-s-triazolo[4,3-a][1,5]benzodiazepin-1,5-(2H,6H)-dione.

EXAMPLE 33

Ethyl 3-[7-trifluoromethyl-4,5-dihydro-4-oxo-5-(o-chlorophenyl)-3H-1,5-benzodiazepin-2-yl]carbazate In the manner given in Example 19, 7-trifluoromethyl-5-(o-chlorophenyl)-2-thio-1H-1,5-benzodiazepin-2,4-(3H,5H)-dione in n-butanol can be refluxed with ethyl carbazate to give ethyl 3-[7-trifluoromethyl-4,5-dihydro-4-oxo-5-(o-chlorophenyl)-3H-1,5-benzodiazepin-2-yl]carbazate.

EXAMPLE 34

8-Trifluoromethyl-6-(o-chlorophenyl-1H-s-triazolo[4,3-a][1,5]benzodiazepin-1,5-(2H,6H)-dione In the manner given in Example 20, 3-[7-trifluoromethyl-4,5-dihydro-4-oxo-5-(o-chlorophenyl)-3H-1,5-benzodiazepin-2-yl]carbazate can be heated to about 250° C. to give 8-trifluoromethyl-6-(o-chlorophenyl)-1H-s-triazolo[4,3-a][1,5]benzodiazepin-1,5-(2H,6H)-dione.

EXAMPLE 35

Ethyl 3-[4,5-dihydro-4-oxo-5-(2,3-dimethylphen;)-3H-1,5-benzodiazepin-2-yl]carbazate In the manner given in Example 19, 7-(2,3-dimethylphenyl)-2-thio-1H-1,5-benzodiazepin-2,4-(3H,5H)-dione in n-butanol can be refluxed with ethyl carbazate to give ethyl 3-[4,5-dihydro-4-oxo-5-(2,3-dimethylphenyl)-3H-1,5-benzodiazepin-2-yl]carbazate.

EXAMPLE 36

6-(2,3-Dimethylphenyl)-1H-s-triazolo[4,3-a][1,5]benzodiazepin-1,5-(2H,6H)-dione

In the manner given in Example 20, 3-[4,5-dihydro-4-oxo-5-(2,3-dimethylphenyl)-3H-1,5-benzodiazepin-2-yl]carbazate can be heated to about 250° C. to give 6-(2,3-dimethylphenyl)-1-H-s-triazolo[4,3-a][1,5]benzodiazepin-1,5-(2H,6H)-dione.

EXAMPLE 37

8-Nitro-1-[(dimethylamino)methyl]-6-(o-chlorophenyl)-4H-s-triazolo[4,3-a][1,5]benzodiazepin-5(6H)-one In the manner given in Example 10, 8-nitro-1-(chloromethyl)-6-phenyl-4H-s-triazolo[4,3-a][1,5]benzodiazepine-5(6H)-one can be reacted with dimethylamine to give 8-nitro-1-[(dimethylamino)methyl]-6-(o-chlorophenyl)-4H-s-triazolo[4,3-a][1,5]benzodiazepin-5(6H)-one.

EXAMPLE 38

8-Trifluoromethyl-2-methyl-6-(o-chlorophenyl)-1H-s-triazolo[4,3-a][1,5]benzodiazepin-1,5-(2H,6H)-dione In the manner given in Example 21, 8-trifluoromethyl-6-(o-chlorophenyl)-1H-s-triazolo[4,3-a][1,5]benzodiazepin-1,5-(2H,6H)-dione can be reacted with sodium hydride and then with methyl chloride to give 8-trifluoromethyl-2-methyl-6-(o-chlorophenyl)-1H-s-triazolo[4,3-a][1,5]benzodiazepin-1,5-(2H,6H)-dione.

In the manner given in the preceding examples 19–38 other compounds of formula IIIB can be produced. Representative compounds thus produced include:

8-methoxy-6-phenyl-1H-s-triazolo[4,3-a][1,5]benzodiazepin-1,5-(2H,6H)-dione;

7-chloro-6-(2-methyl-4-chlorophenyl)-1H-s-triazolo[4,3-a][1,5]benzodiazepin-1,5-(2H,6H)-dione;

8-bromo-6-phenyl-1H-s-triazolo[4,3-a][1,5]benzodiazepin-1,5-(2H,6H)-dione;

8-chloro-6-(o-fluorophenyl)-1H-s-triazolo[4,3-a][1,5]benzodiazepin-1,5-(2H,6H)-dione;

8-chloro-6-(o-ethylphenyl)-1H-s-triazolo[4,3-a][1,5]benzodiazepin-1,5-(2H,6H)-dione;

9-chloro-6-phenyl-1H-s-triazolo[4,3-a][1,5]benzodiazepin-1,5-(2H,6H)-dione;

8-chloro-6-(o-methoxyphenyl)-1H-s-triazolo[4,3-a][1,5]benzodiazepin-1,5-(2H,6H)-dione;

8-chloro-6-(m-chlorophenyl)-1H-s-triazolo[4,3-a][1,5]benzodiazepin-1,5-(2H,6H)-dione;

7-chloro-6-phenyl-1H-s-triazolo[4,3-a][1,5]benzodiazepin-1,5-(2H,6H)-dione;

8-chloro-4-methyl-6-(o-methylphenyl)-1H-s-triazolo[4,3-a][1,5]benzodiazepin-1,5-(2H,6H)-dione;

8-fluoro-2-[(diethylamino)propyl]-6-(o-chlorophenyl)-1H-s-triazolo[4,3-a][1,5]benzodiazepin-1,5-(2H,6H)-dione;

9-trifluoromethyl-2-methyl-6-phenyl-1H-s-triazolo[4,3-a][1,5]benzodiazepin-1,5-(2H,6H)-dione;

8-trifluoromethyl-2-ethyl-6-phenyl-1H-s-triazolo[4,3-a][1,5]benzodiazepin-1,5-(2H,6H)-dione;

8-chloro-2-[(dimethylamino)propyl]-6-(o-fluorophenyl)-1H-s-triazolo[4,3-a][1,5]benzodiazepin-1,5-(2H,6H)-dione;

2-[(dipropylamino)propyl]-6-phenyl-1H-s-triazolo[4,3-a][1,5]benzodiazepin-1,5-(2H,6H)-dione;

2-isopropyl-6-(m-methoxyphenyl)-1H-s-triazolo[4,3-a][1,5]benzodiazepin-1,5-(2H,6H)-dione;

8-fluoro-2-propyl-6-phenyl-1H-s-triazolo[4,3-a][1,5]benzodiazepin-1,5-(2H,6H)-dione;

8-trifluoromethyl-2-[(dimethylamino)propyl]-6-phenyl-1H-s-triazolo[4,3-a][1,5]benzodiazepin-1,5-(2H,6H)-dione;

8-bromo-2-[(dimethylamino)propyl]-6-phenyl-1H-s-triazolo[4,3-a][1,5]benzodiazepin-1,5-(2H,6H)-dione;

8-chloro-2-[(diethylamino)propyl]-6-(o-fluorophenyl)-1H-s-triazolo[4,3-a][1,5]benzodiazepin-1,5-(2H,6H)-dione;

8-chloro-2-[(diethylamino)propyl]-6-(2,4-dimethylphenyl)-1H-s-triazolo[4,3-a][1,5]benzodiazepin-1,5-(2H,6H)-dione;

and the like.

The compound of the foregoing examples and lists, i.e., compounds IIIA, IIIB, IIIC, IIID, IIIE, and IIIF are converted to acid addition salts by reaction with stoichiometrically calculated amounts of selected acids in water, ethanol, or with the hydrogen halides in particular, in ether. In this manner the hydrochlorides, hydrobromides, hydroiodides, sulfates, phosphates, acetates, propionates, lactates, tartrates, citrates, maleates, malates, pamoates, benzenesulfonates, p-toluenesulfonates, methanosulfonates, cyclohexanesulfamates, salicylates and the like of the foregoing 2,4-dihydro-6-phenyl-1H-s-triazolo[4,3-a][1,4]benzodiazepin-1-ones and 3-(5-phenyl-3H-1,5-benzodiazepin-2-yl)carbazic acid alkyl esters are obtained.

I claim:

1. A compound of the formula IIIA

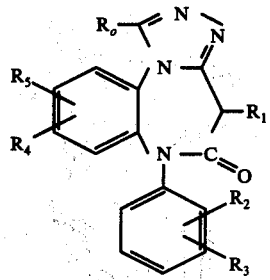

wherein $R_0$ is hydrogen, alkyl of 1 to 3 carbon atoms, inclusive, hydroxy, hydroxymethyl and

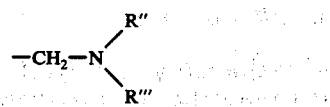

in which R″ and R‴ are hydrogen, alkyl of 1 to 3 carbon atoms or together

is selected from the group consisting of pyrrolidino, piperidino, morpholino, and N-methylpiperazino; wherein $R_1$ is hydrogen or methyl and wherein $R_2$, $R_3$, $R_4$ and $R_5$ are selected from the group consisting of hydrogen, alkyl of 1 to 3 carbon atoms halogen, nitro, trifluoromethyl, alkoxy and alkylthio in which the carbon moieties of alkoxy and alkylthio have from 1 to 3 carbon atoms, inclusive, and the pharmacologically acceptable acid addition salts thereof.

2. A compound of the formula IIIC

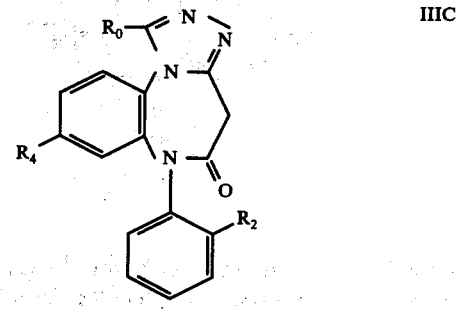

wherein $R_0$ is selected from the group consisting of alkyl of 1 to 3 carbon atoms, inclusive, and

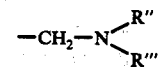

in which R″ and R‴ are hydrogen or alkyl defined as above; wherein $R_2$ and $R_4$ are selected from the group consisting of hydrogen, chlorine, fluorine, bromine, —$CF_3$ and nitro.

3. A compound of the formula IIIE

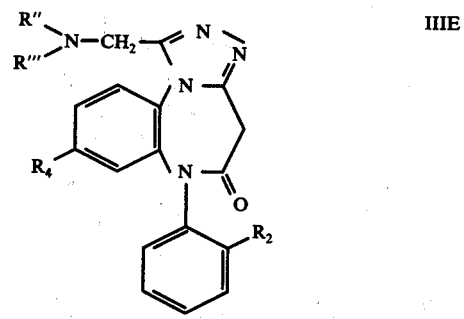

wherein R″ and R‴ are selected from the group consisting of hydrogen and alkyl of 1 to 3 carbon atoms, inclusive; and wherein $R_2$ and $R_4$ are selected from the group consisting of hydrogen and chlorine.

4. A compound according to claim 2 wherein $R_o$ is methyl, $R_2$ is hydrogen, $R_4$ is chloro, and the compound is therefore 8-chloro-1-methyl-6-phenyl-4H-s-triazolo[4,3-a][1,5]benzodiazepin-5(6H)-one.

5. A compound according to claim 2 wherein $R_o$ is methyl, $R_2$ and $R_4$ are chloro and the compound is therefore 8-chloro-1-methyl-6-(o-chlorophenyl)-4H-s-triazolo[4,3-a][1,5]benzodiazepin-5(6H)-one.

6. A compound according to claim 3, wherein R″ and R‴ is methyl, $R_2$ is hydrogen, $R_4$ is chloro and the compound is therefore 8-chloro-1-[(dimethylamino)methyl]-6-phenyl-4H-s-triazolo[4,3-a][1,5]benzodiazepin-5(6H)-one.

7. A compound according to claim 3, wherein R″ and R‴ are methyl, $R_2$ and $R_4$ are chloro and the compound is therefore 8-chloro-1-[(dimethylamino)methyl]-6-(o-chlorophenyl)-4H-s-triazolo[4,3-a][1,5]benzodiazepin-5(6H)-one.

8. A compound of the formula

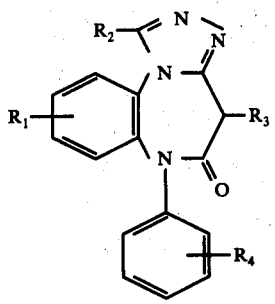

wherein R₁ is a member selected from the group consisting of hydrogen, lower alkyl, halogen, trifluoromethyl, nitro, amino, and lower alkoxy;

R₂ is a member selected from the group consisting of hydrogen and lower alkyl;

R₃ is a member selected from the group consisting of hydrogen or lower alkyl; and R₄ is a member selected from the group consisting of hydrogen, halogen, and lower alkoxy; and the pharmaceutically acceptable acid addition salts thereof.

9. A compound of the formula

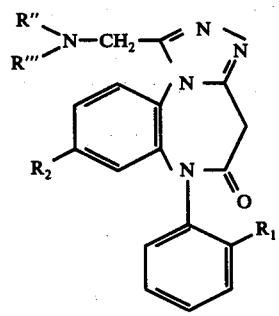

wherein R″ and R‴ is hydrogen or alkyl of 1 to 3 carbon atoms, inclusive, or

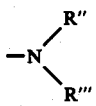

together is pyrrolidino, piperidino, or morpholino; R₁ is hydrogen, chloro, or fluoro; R₂ is hydrogen, chloro, fluoro, nitro, or trifluoromethyl.

10. In a process for the production of a compound of the formula IIIA′

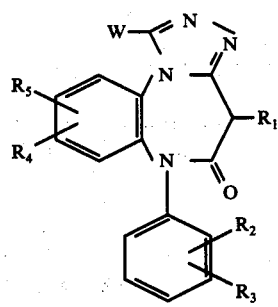

wherein W is selected from the group consisting of alkyl of 1 to 3 carbon atoms, inclusive, hydroxymethyl, and

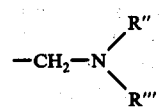

in which R″ and R‴ are hydrogen or alkyl of 1 to 3 carbon atoms; wherein R₁ is hydrogen or methyl; wherein R₂, R₃, R₄ and R₅ are selected from the group consisting of hydrogen, alkyl of 1 to 3 carbon atoms, halogen, nitro, trifluoromethyl, alkoxy, and alkylthio in which the carbon moiety of alkoxy and alkylthio is of 1 to 3 carbon atoms, inclusive, the step which comprises: heating a compound of the formula

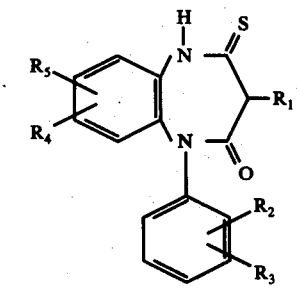

wherein R₁, R₂, R₃, R₄ and R₅ are defined as above, with a reagent compound of the formula

wherein R′ is hydrogen or alkyl of 1 to 2 carbon atoms, to obtain the compound IIIA′ above.

* * * * *